United States Patent
Glasius et al.

(10) Patent No.: US 11,071,318 B2
(45) Date of Patent: Jul. 27, 2021

(54) ENCAPSULATION PROCESS

(71) Applicant: RHODIA OPERATIONS, Paris (FR)

(72) Inventors: Martin Eduard Glasius, Gaillac (FR); Sandrine Emmanuelle Bodin, Garches (FR); Cédric Humblot, Lyons (FR)

(73) Assignee: RHODIA OPERATIONS, Aubervilliers (FR)

( * ) Notice: Subject to any disclaimer, the term of this patent is extended or adjusted under 35 U.S.C. 154(b) by 426 days.

(21) Appl. No.: 15/751,734

(22) PCT Filed: Jul. 28, 2016

(86) PCT No.: PCT/EP2016/068006
§ 371 (c)(1),
(2) Date: Feb. 9, 2018

(87) PCT Pub. No.: WO2017/025342
PCT Pub. Date: Feb. 16, 2017

(65) Prior Publication Data
US 2018/0235268 A1   Aug. 23, 2018

(30) Foreign Application Priority Data

Aug. 10, 2015  (FR) .................................. 1557635

(51) Int. Cl.
| | | |
|---|---|---|
| A23L 27/00 | (2016.01) | |
| A61K 9/16 | (2006.01) | |
| A23P 10/30 | (2016.01) | |
| A23L 2/52 | (2006.01) | |

(52) U.S. Cl.
CPC .............. *A23L 27/72* (2016.08); *A23P 10/30* (2016.08); *A61K 9/1617* (2013.01); *A61K 9/1694* (2013.01); *A23L 2/52* (2013.01); *A23V 2002/00* (2013.01); *A23V 2300/10* (2013.01)

(58) Field of Classification Search
None
See application file for complete search history.

(56) References Cited

U.S. PATENT DOCUMENTS

| | | | | |
|---|---|---|---|---|
| 5,009,900 A | * | 4/1991 | Levine | A23G 3/346 426/103 |
| 5,087,461 A | * | 2/1992 | Levine | A23L 27/72 426/103 |
| 2011/0230565 A1 | | 9/2011 | Le-Thiesse | |
| 2012/0277321 A1 | | 11/2012 | Le-Thiesse et al. | |
| 2014/0031377 A1 | * | 1/2014 | Hafner | A61K 31/11 514/275 |
| 2014/0148507 A1 | | 5/2014 | Ducassou et al. | |

FOREIGN PATENT DOCUMENTS

| | | |
|---|---|---|
| EP | 2868206 A2 | 5/2015 |
| WO | 199406308 A2 | 3/1994 |
| WO | 2002049607 A2 | 6/2002 |
| WO | 2003082247 A2 | 10/2003 |
| WO | 2007117661 A2 | 10/2007 |
| WO | 2008105652 A1 | 9/2008 |
| WO | 2010046239 A1 | 4/2010 |
| WO | 2011042365 A1 | 4/2011 |

OTHER PUBLICATIONS

M. E. Carlotti et al "O/W Microemulsions with vanillin as Vehicles for Antiacne Actives: Preparation, Characterization, and Stability" Journal of Dispersion Science and Technology, Jul. 21, 2008, vol. 29, No. 7, 991-998.

* cited by examiner

*Primary Examiner* — Jenna A Watts
(74) *Attorney, Agent, or Firm* — Osha Bergman Watanabe & Burton LLP

(57) ABSTRACT

The subject-matter of the invention is a process for encapsulating one or more substances with a matrix, wherein said process comprises the preparation of a mixture of said matrix in the liquid state with said substance(s), then the solidification of the mixture obtained, said matrix consisting of vanillin or ethylvanillin or a vanillin/ethylvanillin mixture. The solid compound thus obtained is particularly advantageous in the field of food for human consumption and animal feed, in the pharmaceutical field, as a fragrance in the cosmetics, perfumery and detergence field, or as an encapsulated active ingredient in the pharmaceutical field. The use of a compound chosen form vanillin, ethylvanillin and vanillin/ethylvanillin mixtures as encapsulating agent is also subject-matter of the present invention.

20 Claims, No Drawings

ENCAPSULATION PROCESS

CROSS-REFERENCE TO RELATED APPLICATIONS

The present application is a U.S. national stage entry under 35 U.S.C. § 371 of International Application No. PCT/EP2016/068006, filed Jul. 28, 2016, which claims priority to French Patent Application No. FR1557635 filed on Aug. 10, 2015, the entire content of these applications being incorporated herein by reference for all purposes.

TECHNICAL FIELD OF THE INVENTION

The present invention relates to the technical field of the food industry, and more specifically that of food flavorings and the forming thereof. However, the present invention may have applications outside of this technical field, and apply for example to the forming of pharmaceutical active principles. Other technical fields may be concerned, especially fragrance and cosmetics.

STATE OF THE ART

It is estimated that approximately 20% to 25% of food flavorings sold are in an encapsulated form. The encapsulation of food flavourings is a well-known technique in the technical field. Encapsulation is of use for protecting volatile flavoring substances from evaporation and for protecting oxidizable flavoring substances from degradation which could be caused by the oxygen in the air, heat, humidity or contact with other compounds. There are several encapsulation techniques. Mention may in particular be made of encapsulation by a dissolved material, spray drying, freeze-drying, vacuum drying and fluidized-bed encapsulation. These methods share the fact that they use a material which serves as matrix for the encapsulation of the flavoring. This matrix is conventionally chosen from sugars, such as starches, maltodextrins and other polysaccharides, or gums. International application WO 94/06308 describes, for example, a technique for encapsulating a flavoring in a molten matrix.

One of the problems with encapsulating flavorings lies in the moment of the release of said flavoring during manufacture, storage and consumption of a food product. For example, the customary matrices for encapsulating flavorings are not soluble in chocolate during the preparation steps. At present it is therefore necessary to provide different forms depending on the targeted application.

Moreover, the forming methods alternative to encapsulation in a matrix are not suitable for all flavorings. The flavouring may change and degrade on the support and some notes may evaporate.

It is in this context that the inventors sought a novel forming method, making it possible to overcome one or more of the drawbacks of the current methods.

Vanillin and ethylvanillin are compounds well-known as flavorings in the food sector. On the one hand, numerous documents in the literature propose methods for encapsulating vanilla flavoring. On the other hand, the use of vanillin and ethylvanillin as flavoring or masking agent in solid compositions which may be obtained by encapsulation has been described (see for example International application WO 02/49607). However, the presence of another encapsulating material is necessary. To the knowledge of the inventors, using vanillin or ethylvanillin as encapsulating material has never been described or suggested in the literature.

In the pharmaceutical field, the group TEVA has described, in international applications WO 03/082247 and WO 2007/117661, a pharmaceutical carrier consisting of microparticles of a medicament deposited on support particles. These microparticles are obtained by forming a solid solution of a medicament in a sublimable support on the surface of a support particle, then eliminating said sublimable support. Vanillin is described as being a possible sublimable support. However, this sublimable support is not used as matrix for encapsulating the medicament because it is eliminated. Patent application US 2014/0148507 also describes a solid pharmaceutical composition obtained by melting. However, the concentration of pharmaceutical active principle in the final solid composition is at least 80% by weight, the excipient only representing at most 20% by weight of the final composition.

BRIEF DESCRIPTION OF THE INVENTION

A subject of the invention is a process for encapsulating one or more substances by a matrix, said process comprising the preparation of a mixture of said matrix in the liquid state with said substance(s), then the solidification of the mixture obtained, the concentration of substances encapsulated in the matrix being between 1 ppb and 50% by weight, said matrix consisting of vanillin or ethylvanillin or a vanillin/ethylvanillin equimolar mixture.

Advantageously, said substance(s) may be selected from flavoring compositions, flavor enhancers and pharmaceutical active principles.

According to one embodiment, the step of preparation of the mixture of the matrix with said substance(s) consists in melting said matrix and in mixing said substance(s) with said matrix in the molten state. According to another embodiment, the step of preparation of the mixture of the matrix with said substance(s) consists in mixing said substance(s) with said matrix in the solid state, then in melting the mixture thus obtained. According to yet another embodiment, the step of preparation of the mixture of the matrix with said substance(s) consists in dissolving said matrix in a solvent and in mixing said substance(s) with said dissolved matrix.

The step of solidification may consist of crystallization, bulk solidification, spalling, pelletizing, spray drying, freeze drying, vacuum drying, granulation, fluidized-bed drying, or prilling.

Further, another subject of the invention is the solid compound comprising a matrix in which one or more substances are encapsulated, said matrix consisting of vanillin or a vanillin/ethylvanillin equimolar mixture. This solid compound may advantageously be used as flavoring in the field of human and animal food, of pharmaceuticals, as fragrance in the cosmetics, fragrance and detergent industry, or as encapsulated active principle in the pharmaceutical field.

The use of a compound selected from vanillin, ethylvanillin and vanillin/ethylvanillin mixtures as encapsulant is also a subject of the present invention.

The inventors have observed that the use of a matrix selected from vanillin, ethylvanillin and vanillin/ethylvanillin mixtures enables simple and effective encapsulation of one or more substances of interest, and especially flavoring compounds.

Advantageously, this encapsulation makes it possible to increase the shelf life of said substances. The substance thus encapsulated may be more easily stored. In the case in which the encapsulated substance is a flavoring compound, the encapsulation thereof according to the process of the invention makes it possible to avoid problems of giving off odors and of contaminating other products stored nearby. The improvement in the shelf life may be measured by those skilled in the art by verifying, after a determined storage period, the quality and/or the quantity of the remaining encapsulated substance. This analysis may be carried out qualitatively, for example by organoleptic tests, or else analytically, for example by analysis of gas chromatography type. The increase in the shelf life may be measured in comparison with the same substance formed on any other type of support known to those skilled in the art.

Another advantage of the process according to the invention lies in the fact that the encapsulation matrix is liposoluble. The encapsulated substance will therefore be released in fatty substances. This property is particularly beneficial for use in the field of chocolate making.

Moreover, in the process according to the invention, vanillin, ethylvanillin and vanillin/ethylvanillin mixtures may serve both as flavoring and encapsulation matrix. It is therefore not necessary to add another ingredient, the function of which would merely be to support or encapsulate the flavorings. The final formulation may therefore be more simple, with fewer ingredients, and thus create fewer regulatory constraints.

DESCRIPTION OF THE INVENTION

In the account which follows, the expression "between . . . and . . . " should be understood as including the limits mentioned.

In the process which is the subject of the present invention, vanillin, ethylvanillin or a vanillin/ethylvanillin mixture serve as matrix for the encapsulation of substances. Vanillin, or 4-hydroxy-3-methoxybenzaldehyde, and ethylvanillin, or 3-ethoxy-4-hydroxybenzaldehyde, are products that are widely used in numerous fields of application as flavoring and/or fragrance. The vanillin and ethylvanillin used in the process according to the invention may have been produced via chemical synthesis. Alternatively, the vanillin may have been produced according to a biochemical process, in particular a process of fermentation. Further alternatively, the vanillin may have been extracted from pods. According to a preferred embodiment, the encapsulation matrix is natural vanillin, for example vanillin obtained by a fermentation process or vanillin extracted from pods.

Preferably, the matrix may consist of vanillin or ethylvanillin. The use of a mixture of vanillin and ethylvanillin in any proportions is described here. According to one embodiment, said mixture is an equimolar mixture of vanillin and ethylvanillin. This compound has a melting point of 48° C.-49° C. Other mixtures of vanillin and ethylvanillin are known, especially the mixture of vanillin and ethylvanillin in a vanillin/ethylvanillin mole ratio of 2. This compound has a melting point of 59° C.-60° C. The preparation of such a mixture is described in particular in documents WO 2010/046239 and WO 2011/042365.

The encapsulated substance may be of a different nature. The matrix may serve to encapsulate a single type of substance or else a mixture of several substances. Thus, several different substances may be encapsulated together. The encapsulated substance(s) are necessarily different from the encapsulation matrix.

According to a first embodiment, the encapsulated substance is a flavoring compound. In the following description, the expression "flavoring composition" especially denotes molecules used as flavoring or fragrance which take part in a mechanism in which the organs of taste and/or of smell are involved.

The flavoring compositions may especially be molecules having at least one heteroatom selected from nitrogen, oxygen and sulfur. Said molecules may be cyclic or acyclic, and saturated or unsaturated. Examples of flavoring compounds include alcohols, aldehydes, ketones, esters, ethers, acetates, nitriles, terpenes, nitrogen-based or sulfur-based heterocyclic compounds and essential oils. A flavoring compound may be of natural or synthetic origin. Examples of flavoring compounds may especially be found in the book by S. Arctander, "Perfume and Flavor Chemicals", 1969 and subsequent editions. Further, those skilled in the art may refer to the substances identified by the FEMA GRAS™ programme, and also the substances mentioned in the positive list compiled by the European Union having FLAVIS number (the information system on flavoring substances of the European Union).

More preferably, said flavoring compounds may be selected from saturated and unsaturated aliphatic alcohols, saturated and unsaturated aliphatic aldehydes, saturated and unsaturated aliphatic acetals, saturated and unsaturated aliphatic ketones, saturated and unsaturated aliphatic acids, saturated and unsaturated aliphatic esters, including keto esters and hydroxy esters, saturated and unsaturated aliphatic sulfur-based compounds, including thiols and sulfides, unsaturated aliphatic hydrocarbons, alicyclic ketones, alicyclic enolones, alicyclic esters, alicyclic sulfur-based compounds, terpene alcohols, terpene aldehydes, terpene acetals, terpene ketones, terpene acids, terpene esters, terpene lactones, terpene oxides, aromatic alcohols, aromatic aldehydes, aromatic ketones, aromatic acids, aromatic esters, phenols, phenol esters, aromatic ethers, aromatic oxides, aromatic lactones, aromatic sulfur-based compounds, aromatic nitrogen-based compounds, aromatic hydrocarbons, heterocyclic lactones, heterocyclic esters, furans containing sulfur, furans not containing sulfur, pyrans, dioxolanes, actinidiolides, pyrroles, pyrazines, triazoles, pyridines, oxazoles, pyrimidines, thiophenes, oxathiazines, dithiazines, dithianes and trithianes.

According to this first embodiment, several flavoring compounds are preferably encapsulated in the same matrix. In this case, it is a flavoring composition which is encapsulated. In the remainder of the description, the expression "flavoring composition" especially denotes the formulation of a flavoring by combining several flavoring compounds. A flavoring composition may typically contain between 2 and 100 different flavoring compounds. The flavoring compound and the flavoring composition may optionally be pre-formulated with additives, especially additives which are typical in the field of food-processing, including a support or a solvent.

According to a second embodiment, the substance encapsulated is a flavor enhancer. In the remainder of the description, the expression "flavor enhancer" especially denotes a substance or a set of substances which do not substantially alter the flavor but which increase the intensity thereof.

A flavor enhancer may be of natural or synthetic origin. Among the flavor enhancers, mention may be made of substances such as sodium and potassium salts, for example sodium chloride and potassium chloride, maltol, ethylmaltol, furaneol, sodium L-glutamate (MSG), inosine-5'-monophosphate (IMP), guanosine-5-monophosphate (GMP), hydrolyzed vegetable proteins (HVP), yeast extracts, amino acids and extracts of sauces, such as, for example, stocks, soy sauce, spicy sauces, fish sauce, oyster sauce. Preferably, a flavor enhancer may be selected from sodium and potassium salts, for example sodium chloride and potassium chloride, maltol, ethylmaltol and furaneol. Further, a flavor enhancer may be selected from the substances described in international application WO 2008/105652, and especially in the following group: lactoyl vanillin, lactoyl ethylvanillin, lactoyl isovanillin, lactoyl p-hydroxybenzaldehyde, lactoyl p-hydroxy-m-methoxycinnamaldehyde, lactoyl p-hydroxy-m-methoxycinnamate, lactoyl vanillate, lactoyl homovanillate, lactoyl m-hydroxybenzoic acid, lactoyl isovanillate, lactoyl p-hydroxy-m-methoxyacetophenone, octyl vanillin, decanoyl vanillin, divanillyl succinate, lactoyl o-hydroxy-m-methoxybenzaldehyde, lactoyl eugenol, gluconyl vanillin, and the edible salts and esters thereof.

The encapsulation of a flavor enhancer in a vanillin or ethylvanillin matrix may result in the preparation of a solid compound having an amplified vanillin or ethylvanillin flavor. The solid compound thus obtained is beneficial especially in the food sector since it may be used in the same way as a pure vanillin or ethylvanillin, while delivering a more powerful note. Conversely, a manufacturer may use this compound in a lesser amount while retaining an equivalent strength.

According to a third embodiment, the encapsulated substance is a pharmaceutical active principle. The encapsulation of pharmaceutical active principles is an important technical field in so far as it is essential for the active principle not to be degraded before it is ingested or applied. The use of vanillin or ethylvanillin or the mixture thereof as encapsulation matrix is particularly advantageous in this context since vanillin and ethylvanillin are edible and their flavor may serve to mask an unpleasant taste.

Further, the encapsulated substance may also be selected from additives which can be used in the food sector, such as dyes, antioxidants, preservatives, masking agents, etc., and mixtures thereof in any proportions.

In the process according to the invention, the concentration of the substance encapsulated in the matrix may be between 1 ppb and 50% by weight. When several different substances are encapsulated together, the concentration of each encapsulated substance in the matrix may be greater than or equal to 1 ppb and the sum of the concentrations of all the substances may be less than or equal to 50% by weight.

According to one embodiment, the concentration of encapsulated substance is preferably between 1 ppb and 10% by weight, more preferentially between 10 ppm and 5% by weight. Such concentrations may especially correspond to concentrations of a ready-to-use food flavoring, of use for example in the food-processing industry. According to another embodiment, the concentration of encapsulated substance is preferably between 1% and 50% by weight, more preferentially between 10% and 50% by weight.

In the process according to the invention, the encapsulating matrix preferably represents at least 50% by weight relative to the total weight of the solid compound obtained. Preferably, the encapsulating matrix represents from 50% to 99.9999999% by weight, more preferably from 50% to 99.999%. According to one embodiment, the encapsulating matrix may represent between 90% and 99.9999999% by weight, more preferentially between 95% and 99.999% by weight. According to another embodiment, the encapsulating matrix may represent between 50% and 99% by weight, more preferentially between 50% and 90% by weight.

The encapsulation process according to the invention comprises the preparation of a mixture of said matrix in the liquid state with said substance, then the solidification of the mixture. The mixture thus prepared may therefore be homogeneous or heterogeneous: it may comprise the matrix and the substance to be encapsulated, said matrix being at least partially in liquid form and the substance to be encapsulated being partially or totally in liquid form or partially or totally in solid form.

According to one embodiment of the invention, the step of preparation of the mixture of the matrix with the substance to be encapsulated consists in dissolving said matrix in a solvent and in mixing said substance with said dissolved matrix.

The solvent liable to be used must be chemically inert with regard to vanillin or ethylvanillin, and remain inert during heating in the temperature zone defined below. As solvents liable to be used in the compositions of the invention, use may be made of a polar, protic or aprotic solvent or a mixture of solvents. Non-limiting examples of solvents suitable for the present invention:

water,
alcohols, preferably aliphatic or aryl-aliphatic alcohols, and more preferentially methanol, ethanol, propanol, isopropanol, butanol, phenylethyl alcohol, ethylene glycol, diethylene glycol, propylene glycol, glycerol,
ether-oxides, preferably aliphatic, and more particularly diethyl ether, dipropyl ether, diisopropyl ether, dibutyl ether, methyl tert-butyl ether, ethyl tert-butyl ether, di-tert-butyl ether, ethylene glycol dimethyl ether, diethylene glycol dimethyl ether,
aliphatic, cycloaliphatic or aromatic alkyl or arylalkyl esters of carboxylic acids, preferably alkyl acetates, and more preferentially ethyl acetate, propyl acetate, isopropyl acetate, butyl acetate, and also benzyl salicylate, methyl laurate, methyl benzoate, ethyl citrate, triacetyl glycerol or triacetin, glycerol and acetic acid ester,
ketones, preferably MEK (methyl ethyl ketone),
cyclic or non-cyclic hydrocarbons, preferably cyclohexane,
halogenated solvents, preferably dichloromethane,
supercritical $CO_2$,
and mixtures thereof in any proportions.

Preferably, the solvent is selected from the group consisting of water, ethanol, ethyl acetate, supercritical $CO_2$ and mixtures thereof.

The amount of solvent used depends especially on the nature of the solvent and on the dissolution temperature. Generally, the lower the dissolution temperature, the greater the amount of solvent. The amount of solvent used, expressed by weight relative to the weight of dry matter (matrix+substances to be encapsulated) generally varies between 5% and 99%.

The mixture may optionally be heated to a temperature preferably of between 40° C. and 120° C. and more preferentially between 50° C. and 85° C., to facilitate the dissolution of the vanillin and the ethylvanillin.

According to one embodiment, the solvent is heated beforehand, preferably to between 40° C. and 120° C. and more preferentially between 50° C. and 85° C., then the matrix and the substance(s) to be encapsulated are introduced into the solvent. The mixture is kept stirring for a duration of between 1 second and 120 minutes.

According to another embodiment of the invention, the step of preparation of the mixture of the matrix with the substance to be encapsulated may be carried out without solvent. This embodiment advantageously makes it possible to not have to add additional solvent. The step of preparation of the mixture may consist in melting said matrix and in mixing said substance(s) with said matrix in the molten state, or else in mixing said substance(s) with said matrix in the solid state, then in melting the mixture thus obtained.

This step may consist in loading the matrix and the substance(s) to be encapsulated into a device, separately or as a mixture, and in heating the mixture obtained to a temperature of preferably between 60° C. and 90° C., and more preferably between 70° C. and 80° C. This operation is generally carried out with stirring in any device, especially in a vessel fitted with a conventional heating device, such as, for example, a system of heating via electrical resistances or else via circulation of a heat-transfer fluid in a jacket or else in a heated chamber such as an oven or stove.

Preferably, this molten mixture is prepared under an inert gas atmosphere; this inert gas is preferentially nitrogen. Nonetheless, working under humid air or under dry air is not excluded.

The mixture is kept at the chosen temperature until the molten mixture is obtained.

The step of solidification may be carried out according to any suitable method known to those skilled in the art. It may especially consist of crystallization, bulk solidification, spalling, pelletizing, spray drying, freeze drying, vacuum drying, granulation, fluidized-bed drying, or prilling.

A crystallization may be carried out when the mixing of the matrix with the substance(s) has been carried out in solution in a solvent. Regardless of the preparation variant, the dissolved product may be crystallized according to the conventional techniques of those skilled in the art (by evaporation, by solvent depletion or by cooling), preferably by cooling.

After mixing, the crystallization may be brought about by cooling the solution. If the solution was prepared between 40° C. and 90° C., cooling to room temperature is generally sufficient but cooling may also be carried out to a temperature extending down to 0° C. In the following description, the expression "room temperature" especially denotes a temperature of between 15° C. and 25° C., preferably of between 18° C. and 22° C. If the solution was prepared at room temperature, cooling to a temperature of between 0° C. and 10° C. and more preferentially between 0° C. and 5° C. may be of use for bringing about the crystallization of the compound of the invention. Seeding by introducing seeds into the liquid mixture is possible. Regardless of the preparation variant, the crystallized product may be separated according to conventional liquid/solid separation techniques, preferably by filtration or centrifugation.

When the mixing of the matrix with the substance(s) to be encapsulated has been carried out without solvent, the mixture may be readily bulk solidified. The molten product may be transferred into any container, for example a stainless steel tray which will enable easy recovery of the product after solidification. The cooling of the molten mixture may be carried out by regulation of the cooling temperature by any known means, preferably in the absence of any stirring.

Bulk solidification or solidification by crystallization may be carried out on a suitable inert support to enable easy recovery of the product after solidification. Alternatively, the solidification may take place on a specific support, for example a porous support, which is not intended to be separated from the product after solidification, especially a food support.

The solidified mixture obtained may be formed, and different techniques may be envisaged.

Another forming operation may be carried out by employing the spalling or pelletizing technique on a cylinder or belt. For this purpose, the molten mixture is brought into contact with a cooled metal belt or cylinder, then by scraping the solidified droplets or the film obtained with a knife, the solidified compound is recovered in the form of flakes or pellets.

Steps of post-treatment of the solidified compound may be carried out, for example drying and/or milling.

A drying operation may be carried out in a conventional drying device such as, for example, an oven, a shelf dryer, a fluidized bed, a vacuum oven, etc. The drying may be carried out under air or under an inert gas atmosphere, preferably under a nitrogen atmosphere. The drying may also be carried out in a chamber under reduced pressure, for example under a pressure of between 1.5 Pa and 70 Pa. The drying time may vary from 15 minutes to 2 hours.

Milling may be carried out to obtain particles having a size which is compatible with the envisaged application. The milling operation may be carried out in a conventional apparatus such as a paddle mill, a pin mill or a granulator.

The process according to the invention makes it possible to obtain a solid compound comprising a matrix in which at least one substance is encapsulated. In the present description, the expression "encapsulated" describes all systems, of variable size, form and structure, in which one or more substances are held in a matrix. The inclusion may be homogeneous or heterogeneous, with for example discrete inclusions of substances in the matrix or else a core-shell type structure. The substance may not be totally covered by the matrix. The solidified matrix may be amorphous or crystalline. Optionally, the matrix and the encapsulated substance(s) may co-crystallize.

The composition prepared according to the process of the invention is preferably a divided solid composition, that is to say that it is in a particulate or granular form, granules generally having a greater size than particles. The size of said particles and/or granules ranges, for example, between 10 µm and 60 000 µm and preferably between 500 µm and 1000 µm. The particles may also have a platelet form, these particles being referred to as "flakes", having a length of between 0.5 and 6 cm, preferably between 1 and 3 cm, a width of between 0.5 and 3 cm, preferably between 0.5 and 1.5 cm, and a thickness of between 400 µm and 1500 µm, preferably between 500 µm and 750 µm. After milling, the particle size expressed by the median diameter ($d_{50}$) may range from 200 µm to 1000 µm and is preferably between 500 µm and 800 µm. The median diameter is defined as being such that 50% by weight of the particles have a diameter greater or less than the median diameter.

One of the advantages of the solid compound according to the invention is the homogeneous dispersion of the substance to be encapsulated in the matrix. Indeed, when the amounts of substances required for a use are very low, it may be difficult to correctly disperse this substance. This is the case for example for a flavoring in a food preparation. The encapsulation of this substance in a vanillin or ethylvanillin matrix makes it possible to pre-disperse said substance in a solid compound, which is subsequently easier to use.

The solid compound according to the invention may be used in numerous fields of application. It is highly advantageously used as flavoring in the field of human and animal food, of pharmaceuticals, as fragrance in the cosmetics, fragrance and detergent industry, and as encapsulated active principle in the pharmaceutical field.

The solid compound according to the invention is particularly suitable for the chocolate making field, regardless of the form of implementation: bars of chocolate, couverture chocolates, filling for chocolates. Indeed, the vanillin or ethylvanillin matrix has the advantage of being soluble in chocolate. The compound according to the invention may therefore solve the technical problem of releasing flavorings in chocolate. The compound according to the invention may be introduced during the tempering step or during the conching step, i.e. the blending of the cocoa paste with the various ingredients, especially the flavorings, or after conching, by using it in cocoa butter. In this field of application, the composition according to the invention is used according to the type of chocolate, at an amount from 0.0005 g to 1 g per 1 kg of finished product: the highest contents being found in couverture chocolate.

Another preferred field of application of the compound according to the invention is that of biscuit and patisserie confectionery, and more particularly:
- dry biscuits: sweet biscuits of standard type, butter-based biscuits, "galette" biscuits, snack biscuits, shortbread biscuits;
- industrial patisserie: ladyfinger biscuits, cat's tongue biscuits, sponge finger biscuits, sponge cake, genoise sponge cake, madeleines, pound cake, loaf cakes, almond-based patisserie, petits-fours.

The fundamental elements present in the mixtures intended for the abovementioned industries are proteins (gluten) and starch, which are usually provided by wheat flour. For the preparation of the various types of biscuits and cakes, ingredients such as sucrose, salt, eggs, milk, fat, optionally chemical raising agents (sodium bicarbonate or other artificial raising agents) or biological yeasts and various cereal flours, etc., are added to the flour.

The incorporation of the compound according to the invention is performed during the manufacture, as a function of the desired product, and is carried out according to the standard techniques of the field under consideration (cf. especially J. L. Kiger and J. C. Kiger—Techniques Modernes de la Biscuiterie, Pâtisserie-Boulangerie industrielles et artisanales [*Modern techniques of biscuit confectionery, industrial and artisanal pastry making and bakery*], Dunod, Paris, 1968, Volume 2, pp. 231 et seq.). Preferentially, the compound according to the invention is introduced into the fat incorporated into the preparation of the dough. By way of indication, it will be specified that the compound according to the invention is introduced in an amount of from 0.005 g to 1 g per kg of dough.

Another use of the compound according to the invention is the production of filling for biscuits or confectioneries.

Yet another use of the compound according to the invention is the production of candies of any type: sugar-coated candies, caramels, nougats, hard candies, soft candies and the like. The amount of compound according to the invention introduced into the products containing it depends on the more or less pronounced taste that is desired. Thus, the doses used may range between 0.001% and 0.2% by weight of the product in which the compound is present. The contents to be used are generally low, of the order of 0.02 g per 1 kg of final product.

The compound according to the invention is also suitable for uses in the dairy industry and more particularly in flavored and gelled milks, entremets, yoghurts, ices and ice creams. Flavoring is performed by simple addition of the compound according to the invention, into one of the mixing stages required during the production of the product containing said compound.

The compound according to the invention may also be used in the preparation of vanillin-containing sugar, that is to say the impregnation of sugar with said compound, at an amount of the order of 7 g expressed relative to 1 kg of finished product.

The compound according to the invention may also be incorporated into various drinks. Mention may be made, inter alia, of grenadine and chocolate-based drinks. In particular, it may be used in preparations for instant drinks dispensed by automatic drink dispensers, flavored powdered drinks or chocolate powder, or alternatively in instant preparations in powder form intended for making desserts of any type, flans, cake batter or pancakes, after dilution with water or milk.

Another field of application of the compound according to the invention is that of animal food, especially for the preparation of meal for calf and pig feed. The recommended content is about 0.2 g per kg of meal to be flavored.

The compound according to the invention may find other applications, such as a masking agent for the pharmaceutical industry (masking the odor of a medicament) or for other industrial products (such as gum, plastic, rubber, etc.).

It is entirely suitable in totally different fields such as cosmetics and the fragrance or detergent industry. It may be used in cosmetics such as creams, milks, face powders and other products and also, as fragrancing ingredients, in fragrancing compositions and fragranced substances and products. The term "fragrancing compositions" denotes mixtures of various ingredients such as solvents, solid or liquid supports, fixing agents, various odorizing compounds, etc., into which the compound according to the invention is incorporated, which compound is used to give various types of finished products the desired fragrance. Perfume bases constitute preferred examples of fragrancing compositions in which the composition prepared according to the process of the invention may advantageously be used in a content of from 0.1% to 2.5% by weight. Perfume bases may serve for the preparation of numerous fragranced products, for instance eau de toilettes, perfumes, aftershave lotions; toiletry and hygiene products such as bath or shower gels, deodorant or antiperspirant products, whether in the form of sticks or lotions, talcs or powders of any nature; hair products such as shampoos and haircare products of any type. Another example of the use of the compound according to the invention is the field of soapmaking. It may be used in a content of from 0.3% to 0.75% of the total mass to be fragranced. Generally, it is combined in this application with benjoin resinoid and sodium hyposulfite (2%).

The compound according to the invention may find numerous other applications, especially in room air fresheners or any maintenance product.

In addition, the solid compound according to the invention may be used in the pharmaceutical field, especially when the encapsulated substance is a pharmaceutical active principle.

Example

Vanillin was weighed into a reactor and melted at a temperature of 85° C.-90° C. A mixture of several flavoring compounds was weighed and added to the molten vanillin. The mixture was homogenized by stirring by means of a spatula for approximately 5 seconds while keeping the temperature at 85° C.-90° C. The liquid mixture thus obtained was poured onto a stainless steel tray and left to cool to room temperature, i.e. for approximately 15/20 minutes per 20 g of molten mixture. A solid sheet was obtained. This sheet was broken, then milled by means of a mill for 20 seconds at room temperature.

A fine powder was obtained. The latter is formed of vanillin in which the flavoring compounds are encapsulated.

The invention claimed is:

1. A process for encapsulating one or more substances by a matrix, comprising:
   preparing a mixture of said matrix in the liquid state with said one or more substances, and solidifying the mixture thus obtained,
   wherein the concentration of the one or more substances encapsulated in the matrix is between 1 ppb and 50% by weight of the total weight of the matrix and one or more encapsulated substances, and said matrix consists of vanillin or ethylvanillin or a vanillin/ethylvanillin equimolar mixture, wherein the one or more substances are selected from the group consisting of flavoring compositions, flavor enhancers, and pharmaceutical active principles.

2. The process as claimed in claim 1, wherein the matrix is natural vanillin.

3. The process as claimed in claim 1, wherein the step of preparing the mixture of the matrix in the liquid state with said one or more substances comprises:
   melting said matrix, and
   mixing said one or more substances with said matrix in the molten state.

4. The process as claimed in claim 1, wherein the step of preparing the mixture of the matrix in the liquid state with said one or more substances comprises:
   mixing said one or more substances with said matrix in the solid state, and melting the mixture thus obtained.

5. The process as claimed in claim 1, wherein the step of preparing the mixture of the matrix in the liquid state with said one or more substances comprises:
   dissolving said matrix in a solvent, and
   mixing said one or more substances with said dissolved matrix.

6. The process as claimed in claim 1, wherein the step of solidifying the mixture comprises crystallization of, bulk solidification of, spalling, pelletizing, spray drying, freeze drying, vacuum drying, granulation, fluidized-bed drying, or prilling the mixture.

7. The process as claimed in claim 1, further comprising one or more steps, subsequent to the step of solidifying the mixture, selected from drying and milling the mixture.

8. The process as claimed in claim 1, further comprising a step, subsequent to the step of solidifying the mixture, of drying the mixture in an oven, a shelf dryer, a fluidized bed, or a vacuum oven.

9. The process as claimed in claim 1, further comprising a step, subsequent to the step of solidifying the mixture, of milling the mixture in a paddle mill, a pin mill, or a granulator.

10. A solid compound, comprising a matrix consisting of vanillin or a vanillin/ethylvanillin equimolar mixture, and one or more substances encapsulated in the matrix, wherein the concentration of encapsulated substances in the matrix is between 1 ppb and 50% by weight of the total weight of the matrix and one or more encapsulated substances, wherein the one or more substances are selected from the group consisting of flavoring compositions, flavor enhancers, and pharmaceutical active principles.

11. The solid compound as claimed in claim 10, wherein the matrix is natural vanillin.

12. The solid compound as claimed in claim 10, wherein the solid compound is in the form of particles or granules, the size of which is between 10 μm and 60 000 μm.

13. The solid compound as claimed in claim 12, wherein the solid compound is in the form of particles having a median diameter ($d_{50}$) of which is between 200 μm and 1000 μm.

14. The solid compound as claimed in claim 10, wherein the solid compound is in the form of flakes.

15. The solid compound as claimed in claim 14, wherein the flakes have:
    a length of between 0.5 cm and 6 cm,
    a width of between 0.5 cm and 3 cm, and
    a thickness of between 400 μm and 1500 μm.

16. A solid compound, comprising a matrix consisting of vanillin or a vanillin/ethylvanillin equimolar mixture and one or more substances encapsulated in the matrix, wherein the solid compound is made by the process as defined in claim 1, wherein the one or more substances are selected from the group consisting of flavoring compositions, flavor enhancers, and pharmaceutical active principles.

17. A composition, comprising the solid compound as claimed in claim 10, wherein:
    the compound is a flavoring and the composition is selected from human food compositions, animal food compositions, and pharmaceutical compositions,
    the compound is a fragrance and the composition is selected from cosmetic compositions, fragrance compositions, and detergent compositions, or
    the compound is an encapsulated active principle and the composition is a pharmaceutical composition.

18. The composition as claimed in claim 17 wherein the compound is a flavoring and the composition is a chocolate composition.

19. The solid compound as claimed in claim 13, wherein the solid compound is in the form of particles having a median diameter ($d_{50}$) of which is between 500 μm and 800 μm.

20. The solid compound as claimed in claim 15, wherein the flakes have:
    a length of between 1 cm and 3 cm,
    a width of between 0.5 cm and 1.5 cm, and
    a thickness of between 500 μm and 750 μm.

* * * * *